United States Patent [19]
Trudell et al.

[11] Patent Number: 5,207,705
[45] Date of Patent: May 4, 1993

[54] PROSTHESIS OF FOAM POLYURETHANE AND COLLAGEN AND USES THEREOF

[75] Inventors: Leonard A. Trudell, East Grenwich, R.I.; Anthony D. Whittemore, Sherborn, Mass.

[73] Assignee: Brigham and Women's Hospital, Boston, Mass.

[21] Appl. No.: 721,461

[22] PCT Filed: Dec. 8, 1989

[86] PCT No.: PCT/US89/05481

§ 371 Date: Jun. 28, 1991

§ 102(e) Date: Jun. 28, 1991

Related U.S. Application Data

[63] Continuation-in-part of Ser. No. 281,364, Dec. 8, 1988, abandoned.

[51] Int. Cl.$^5$ ............................................. A61F 2/06
[52] U.S. Cl. ................................... 623/1; 623/11; 623/66; 602/46; 521/55; 521/905
[58] Field of Search .............. 623/1, 11, 66; 128/832, 128/833; 602/46; 604/368, 369; 521/55, 905, 906

[56] References Cited

U.S. PATENT DOCUMENTS

| | | | |
|---|---|---|---|
| Re. 31,618 | 7/1984 | Mano et al. | 3/1.4 |
| 4,327,195 | 4/1982 | Cioca et al. | 521/102 |
| 4,393,871 | 7/1983 | Vorhauer et al. | 604/58 |
| 4,601,714 | 7/1986 | Burnhill | 604/286 |
| 4,627,836 | 12/1986 | MacGregor | 424/423 |
| 4,655,980 | 4/1987 | Chu | 264/102 |
| 4,670,014 | 6/1987 | Huc et al. | 604/891 |
| 4,687,482 | 8/1987 | Hanson | 623/1 |
| 4,690,973 | 9/1987 | Noishiki et al. | 525/54.1 |
| 4,699,141 | 10/1987 | Lamberton et al. | 523/114 |
| 4,711,783 | 12/1987 | Huc et al. | 424/460 |
| 4,773,409 | 9/1988 | Cilento et al. | 128/156 |
| 5,002,583 | 3/1991 | Pitaru et al. | 623/66 |

FOREIGN PATENT DOCUMENTS

| | | |
|---|---|---|
| 0058623 | 8/1982 | European Pat. Off. |
| 1494939 | 6/1969 | Fed. Rep. of Germany |
| 2092894 | 8/1982 | United Kingdom ................. 623/1 |

OTHER PUBLICATIONS

M. H. Lipsky et al., *J. Biomed. Mater. Res.*, 23:1441-52 (1989).
J. S. Hanker et al. *Science* 242:885-892 (1988).
C. G. Gebelein, "Prosthetic and Biomedical Devices" in: Kirk-Othmer Concise Encyclopedia of Chemical Technology M. Grayson, ed., John Wiley & Sons, 1985 pp. 965-968.
A. Huc, *J. Am. Leather Chemists Assoc.*, 80:195-212.
P. Maurer et al., *Eur. Surg. Res.* Sep.-Oct.:90 (1983).
M. Tachibana et al., *J. of Urology* 133:866-869 (1985).
H. Sanders et al., *Chem. Eng. News*, Apr. 1, 1988, pp. 30-40, continued on 44-45 and 47-48.
H. Grillo, et al., *J. Surg. Res.* II(1):69-82 (Jan. 1962).
A. Robert et al., *Pathol. Biol.* (Paris) 24 (Supp):42-47 (1976).
B. W. Vorhauer, *Biofluid Mechanics* 2:93-124 (1980).
P. Lamberton et al., *ASAIO Abstracts* 16:29 (1987).
S. Shindo, et al., *Jour. of Vascular Surgery* 6:325-332 (1987).
Chaikof et al., *J. Surg. Res.* 47(3):193-199 (1989).
Abbott et al., *J. Vasc. Surg.* Symposium: Fundamental Problems in Vascular Surgery II, 5(2):376-382 (1987).

*Primary Examiner*—Paul Prebilic
*Attorney, Agent, or Firm*—Sterne, Kessler, Goldstein & Fox

[57] ABSTRACT

An implantable medical prosthesis is provided having a uniform mixture of foam polyurethane and collagen. The prosthesis can be shaped into an elongated hollow body tube useful for implantation in an animal. Alternatively, the prosthesis can be shaped into biocompatible units useful as soft-tissue replacements or as matrices for sustained-release vehicles.

15 Claims, 2 Drawing Sheets

POLYURETHANE/COLLAGEN GRAFT PROTOTYPES (MODEL 2)

PROSTHESIS OF FOAM POLYURETHANE AND COLLAGEN AND USES THEREOF

CROSS-REFERENCE TO RELATED APPLICATIONS

This application is a continuation-in-part of U.S. patent application Ser. No. 07/281,364 filed Dec. 8, 1988, now abandoned.

FIELD OF THE INVENTION

The present invention is in the field of medical prostheses. More specifically, the present invention is directed to a prosthesis composed of a uniform mixture of collagen and foam polyurethane which is suitable for use, for example, as a vascular prosthesis or soft tissue replacement.

BACKGROUND OF THE INVENTION

The use of prostheses for the replacement of blood vessels and other anatomical ducts is of great interest in medicine and veterinary work. The use of biomaterials in prostheses and biomedical devices is reviewed in Hanker, J. S. et al., *Science* 242:885-892 (1988), and by Gebelein, C. G., "Prosthetic and Biomedical Devices" in Kirk-Othmer, *Concise Encyclopedia of Chemical Technology*, M. Grayson, ed., Wiley & Sons, 1985, pp. 965-968, both incorporated herein by reference. To be acceptable in a given application, a prosthesis must exhibit the proper mechanical properties and bio-acceptable composition for the given application. For example, vascular prostheses must provide a bio-acceptable surface which is conducive to cellular attachment and sustained blood flow, but yet is strong enough not to split or tear. Especially it is critical that the vascular prosthesis not tear along the body of the prosthesis or at the site of the sutures.

Collagen has been proposed as a biomaterial which has many properties desirable of a medical prosthesis. Collagen is a family of fibrous proteins that have been classified into a number of structurally and genetically distinct types (Stryer, L. *Biochemistry*, 2nd Edition, W. H. Freeman & Co., 1981, pp. 184-199).

Type I collagen is the most prevalent form. Type I collagen is found in skin, tendons, and bones and consists of two subunits of $\alpha 1(I)$ collagen and one subunit of a different sequence termed $\alpha 2$. Other types of collagen have three identical subunits or chains, each consisting of about 1,000 amino acids.

Different tissues express different types of collagen, depending upon their structural needs. For example, type II collagen is found in cartilage, type III collagen is found in blood vessels and the cardiovascular system, and type IV collagen is localized in basement membranes. Collagen is a unique protein in that it forms insoluble fibers that have a high tensile strength.

Tubes made of pure collagen have been proposed for use as vascular prostheses (Noishiki, Y. et al., U.S. Pat. No. 4,690,973; Chu, G. U.S. Pat. No. 4,655,980; and Huc, A. *J. Am. Leather Chem. Assoc.* 80:195-212 (1985)); arterial prostheses (Maurer, P. et al., *Eur. Surg. Res.* Sep.–Oct., p. 90, (1983)); ureteral replacements, (Tachibana, M. et al., *J. Urology* 133:866-869 (1985)); and as a microencapsulation material for the oral administration or implantation of controlled release substances (Huc, A., et al., U.S. Pat. Nos. 4,711,783 and 4,670,014; Sanders, N. J., *Chem. Eng. News*, Apr. 1, 1985, p. 30-48).

However, the mechanical properties of prostheses made solely of collagen are not satisfactory for many purposes due to a tendency to tear or split. Especially, prostheses made solely of collagen are not satisfactory for replacement of vessels with a small diameter (Huc, A., *J. Am. Leather Chem. Assoc.* 80:195-212 (1985)). Attempts to strengthen the mechanical characteristics of collagen by fixing or tanning it have not been successful. Grillo found collagen tubes too weak to allow fine silk suturing without splitting at the sites of the needle puncture (Grillo, H. C. et al., *J. Surg. Res II* (1): 69-82 (1962)).

To avoid the mechanical deficiencies of collagen tubular prostheses, prostheses composed of other polymers such as Dacron and polyurethane have been prepared (Robert, A.-M. et al., *Pathol. Biol. (Paris)* 24-Supp.:42-47 (1976); Maupepit, P., EP Patent Application Publication No. 058623); as well as combinations of plastics and polyurethane (Hanson, S. R., U.S. Pat. No. 4,687,482; Mano, H. et al.. U.S. Pat. No. Re. 31,618; and Buddecke, E., DE Patent No. 1,494,939). However, these prostheses lack the biocompatability of collagen, and do not promote the revascularization of the prosthesis in the manner that collagen does (Huc, A., *J. Am. Leather Chem. Assoc.* 80: 195-212 (1985)). In addition, prostheses made solely from synthetic materials often evoke a foreign body response, suffer from fatigue or are potentially toxic or carcinogenic (Grillo, H. C. et al., *J. Surg. Res. II* (1):69-82 (1982)).

A composition comprising foam polyurethane and collagen has been used as a contraceptive sponge (Vorhaur, B., *Biofluid Mechanics*, vol. 2, 1980, Plenum, pp. 93-124) and to promote neovascularization (Lamberton, P. et al., *ASAIO Abstracts* 16:29 (1987)). Lamberton also proposed the use of a collagen impregnated polyurethane sponge to promote neovascularization in endocrine or hepatic transplantation, soft tissue prosthesis, bone graft or drug delivery systems (Lamberton, P. et al., *ASAIO Abstracts* 16:29 (1987)).

But there remains a need for a prosthesis which provides the bio-compatibility of collagen with the required pliancy and mechanical strength for use in medical applications such as conduits for the replacement of a missing, diseased or damaged biological vessel and especially a biological vessel with a small diameter.

SUMMARY OF THE INVENTION

The present invention provides a composition comprising foam polyurethane and collagen which can be shaped into biocompatible units for implantation as prostheses wherein the collagen is an integral part of the matrix which forms the backbone of the prosthetic structure.

The present invention further provides a tubular prosthesis useful for implantation in an animal comprising an elongated hollow body tube, said hollow body tube being open at both ends and defining a confined-flow passageway, wherein said prosthesis comprises a uniform mixture of foam polyurethane and collagen, of one or more layers; the vascular prosthesis so produced has the strength and pliancy consistent with replacement of the human artery.

The present invention further provides a composition of collagen and foam polyurethane that can be shaped into biocompatible units, of one or more layers, for use as soft-tissue replacements or as matrices for sustained-release vehicles. Such biocompatible units may also supply medicinal substances such as hormones or drugs at a controlled rate to the host.

DETAILED DESCRIPTION OF THE INVENTION

Figure 1:
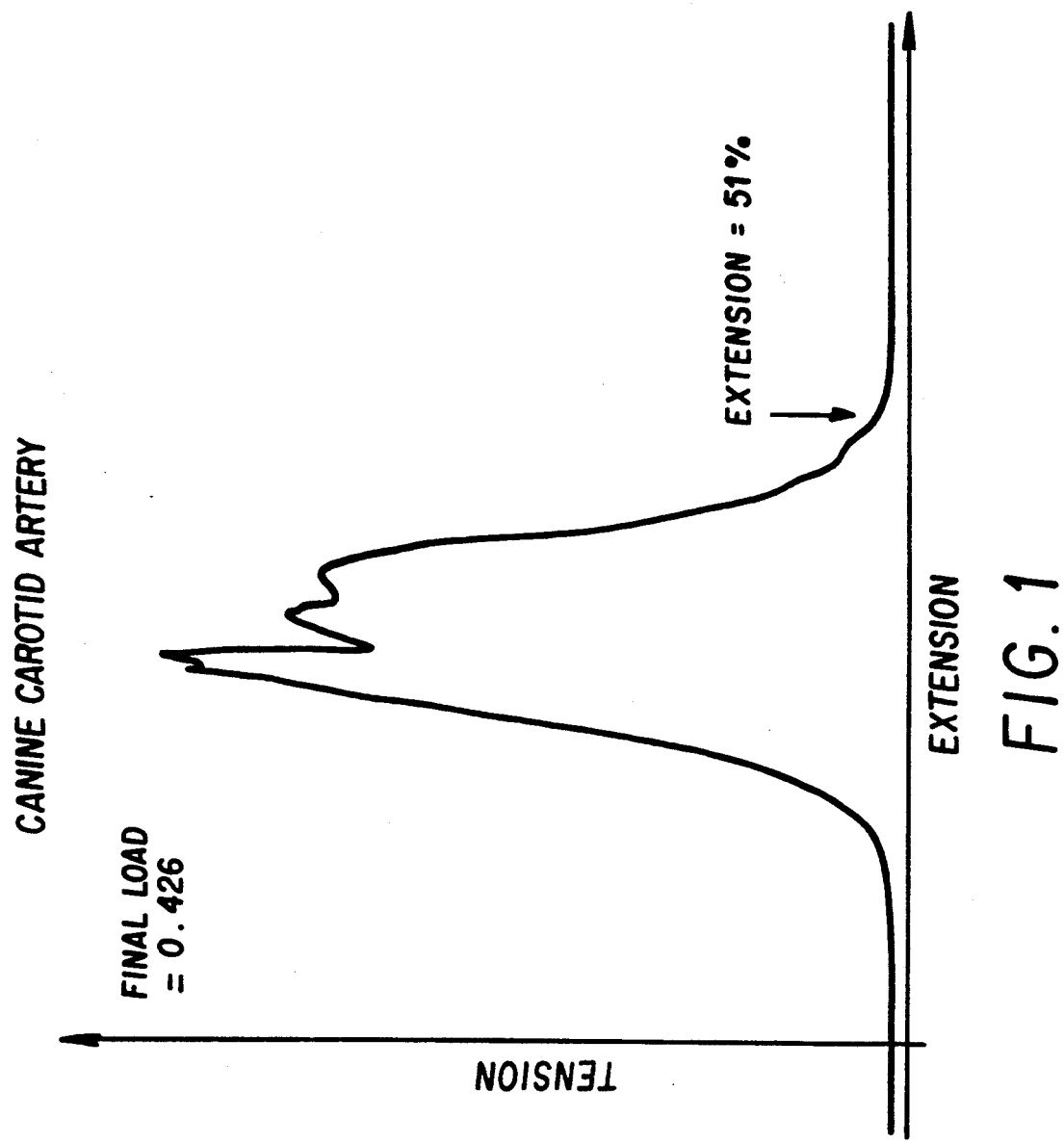
FIG. 1 is a graph representative of a typical tensile strength response of a canine carotid artery.

The invention provides a composition comprising a mixture of foam polyurethane and collagen which is capable of being shaped into a wide variety of bio-compatible conduits and especially into a tube, suitable for implantation as an artificial device, a prosthesis, to replace a missing, diseased or damaged part of the body of a human or other animal. Additionally this composition of foam polyurethane and collagen is capable of forming a vascular prosthesis with mechanical characteristics consistent with replacement of the human artery. Additionally, this composition of foam polyurethane and collagen is capable of forming implantable biocompatible units capable of use as soft-tissue replacements and as sustained-release vehicles.

The prosthesis composition of the present invention derives from the inventors' discovery that foam polyurethane is capable of correcting the mechanical deficiencies of collagen prostheses. The prostheses of the invention, comprising a mixture of foam polyurethane and collagen, for the first time allow the implantation of a prosthesis with the bio-compatibility advantages of collagen and the mechanical advantages of polymerized foam polyurethane. The incorporation of collagen during the cross-linking reaction makes collagen an integral chemical component of the structure of the molded polyurethane prosthesis. Surprisingly, unexpected and advantageous mechanical properties are realized when collagen is incorporated into the polyurethane matrix as the prosthesis is formed. These unexpected and advantageous mechanical properties include unexpected strength and resistance to tearing at the site of the sutures.

By prosthesis is meant an artificial device designed to replace a missing, diseased or damaged part of the body of an animal.

By a prosthesis containing at least one "layer" of the composition of the invention (a uniform mixture of foam polyurethane and collagen) is meant a prosthesis containing at least one discrete ply or strata of the composition of the invention. This layer may be joined, in the final product, to additional layers wherein each layer surrounds the other but wherein each layer, that is each ply or stratum, had originally been molded separately or at a separate time, from the other layers. The layers containing the composition of the invention may be directly adjacent to each other or physically separated by a layer(s) of a substance with a differing composition. A layer or layers of a substance with a composition different from that of the composition of the invention may also be used to "coat" the prosthesis on its inner and/or outer surface. For example, the layered prosthesis may be molded so as to contain an outer layer containing polyurethane and silicone.

By animal or host is meant a human or other member of the kingdom Animelia which is developed enough to have separate organ systems and a circulatory system.

By biocompatible is meant compatible with living tissue; a biocompatible substance does not harm the host nor does it evoke a severe foreign body reaction. In a severe foreign body reaction, the function of the prosthesis becomes severely compromised by the host's response to its presence.

By implant is meant to fix or set securely in a living site, such as in tissue or as a replacement for a biological vessel or conduit, a prosthesis which promotes tissue growth, slow release of a medicinal substance, or formation of an organic union with the surrounding tissue.

By conduit is meant a channel through which something (as a fluid) flows or is conveyed.

By tubular is meant the form of a tube; that is, resembling a hollow, sometimes elongated, cylinder. When the prosthesis of the invention is in the shape of a hollow tube, it has an inner and an outer surface; the inner surface being that surrounding the liquid being conveyed through the prosthesis.

By uniform mixture is meant a mixture which has the same composition or physical properties throughout the entire physical structure of the mixture.

By sustained-release vehicle is meant a biocompatible vehicle capable of supplying a prolonged release of substance such as a drug or hormone, for a relatively long period of time, such as hours, days, months or even years.

The chemistry of the urethanes is reviewed in Billmeyer, F. W., *Textbook of Polymer Science*, Wiley & Sons, 1984, incorporated herein by reference. Polyurethanes are polymers containing the group:

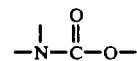

and are typically formed through the reaction of a diisocyanate and a glycol:

In the production of polyurethane foams, excess isocyanate groups in the polymer react with water or carboxylic acids to produce carbon dioxide which 'blows' the foam at the same time that crosslinking is occurring. This results in a crosslinked product containing bubbles of trapped carbon dioxide. As discussed in Billmeyer, supra, upon curing, the polyurethane foam may be either flexible or rigid depending on the nature of the polymer and the type of crosslinking. Because of the rapid curing of the polyurethane, it is especially compatible with reaction injection molding (RIM) wherein the polymerization and crosslinking are effected simultaneously with molding of the material into its final shape.

Urethane foams are made in several steps. First, there is a basic intermediate which comprises a polyether made of poly(1,4-butylene glycol), sorbitol polyether, or other polyethers of a molecular weight around 1,000 daltons. If flexible foams are desired, this intermediate is bifunctional and if rigid foams are desired this intermediate is polyfunctional.

The basic intermediate reacts with an aromatic diisocyanate, usually tolylenediisocyanate, to give a prepolymer. Catalysts are then added to the prepolymer to effect rapid production of foam as described above with crosslinking forming through the synthesis of urea bridges. Crosslinking increases the melting point, decreases the solubility and moisture regain and strengthens the interstrand bonding.

In some cases, a low-boiling inert liquid such as a fluorocarbon has been used to replace the blowing action of carbon dioxide. This results in a foam with some altered characteristics, such as a lower thermal conductivity due to the entrapped fluorocarbon gas, when compared to the carbon dioxide blown foams. Alternatively, a two-step synthesis may be used, wherein the foam is first partly frothed with the inert gas and then foamed with carbon dioxide.

In the one-step process for the synthesis of flexible foams, the polyether intermediate tolylenediisocyanate and catalysts are mixed just before foaming.

Hypol 2002 (sold by W. R. Grace and Co., Lexington, Mass.) is preferred because it is a special medical grade of polyurethane prepolymer which, upon mixing with water and other aqueous solutions, produces a hydrophilic foam having no extractable toluene diamine, toluene disocyanate or other primary aromatic amines. Foam extracts of this product are inert in the body and are not mutagenic. In addition, the cured product has been shown to be a good biomaterial for supporting cellular growth and, potentially, a good biomaterial to serve as a blood/surface interface. Hypol is described in U.S. Pat. No. 4,127,200, incorporated herein by reference. An elastic biomaterial is necessary for the fabrication of implantable medical devices such as vascular grafts, small diameter vascular grafts, atrial patches, ventricular patches, prosthetic valve cusps and arterial patches.

Additionally, the foamed polyurethane (polyurethane isocyanate) may be manufactured such that the end product may be biodegradable, thus allowing the product to be slowly absorbed by the host. The material can be engineered to any point along a scale of from rapidly biodegradable to biodurable where biodurable is defined as a substance as stable as Dacron in the host. Biodegradability, of the final polymer, is determined by the inclusion, in the reacting liquid, of chemical species (or groups) that are scissionable (or "digestible") in a living mammalian system. An example of how to increase the biodegradability of the final polymer would be to react the Hypol with lactic acid groups that can be broken down in vivo. In that example, the total number of scissionable lactic acid bonds per unit material would determine the time course of degradation.

Any non-antigenic, non-specific collagen such as, for example, a synthesized collagen is useful in the invention. When used as a vascular graft, type III collagen is preferred because it is the type of collagen native to blood vessels. Vascular collagen (type III) can be obtained commercially from Sigma Chemical Company, St. Louis, Mo. The collagen solution is dissolved in 0.005M acetic acid solution. The collagen goes into solution readily, in the cold (4°-6° C.) in 24-48 hours.

The prosthesis described herein has at least three essential characteristics. First, the prosthesis is compatible with animal tissues and does not provoke a severe foreign body reaction. Second, the prosthesis is strong enough to a) resist tearing at the site of suture and b) resist splitting due to physiological pressures of a liquid such as blood being conveyed through it. Third, the prosthesis potentially promotes neovascularization of the implant site and may provide a surface conducive to the ingrowth and proliferation of cells from adjacent areas and the development of new tissue. These three characteristics are achieved by including collagen in the reaction mixture at the time of chemical cross-linking of the polyurethane during formation or molding of the prosthetic structure.

The present invention further provides a tubular prosthesis useful for implantation in an animal comprising an elongated hollow body tube, said hollow body tube being open at both ends and defining a confined-flow passageway.

In a preferred embodiment, the confined-flow passageway of said prosthesis has an inner diameter of 10 mm or less.

In another preferred embodiment, the confined-flow passageway of said prosthesis has an inner diameter of 5 mm or less.

Especially, the composition is compatible with grafts of a small diameter; that is, with a graft having an inner diameter of 5.0 mm or smaller. A standard size graft of 6.0 mm or greater such as those commonly used in clinical peripheral vascular surgery is also compatible with the composition of the invention.

Preferably, the prepolymer is Hypol 2002 and is mixed with a stock solution of saline or Lactated Ringer's Solution containing 1. 0 mg/ml collagen, 2 units/ml heparin, and 2 ml of 0.1%/liter of Triton X-100 as a surfactant. The use of 2 ml/liter of 0.1% Triton X-100 as a surfactant ensures that the polyurethane has closed-cell foam when activated as described below. Lactated Ringer's solution U.S.P. is composed of 600 mg of sodium chloride; 300 mg of sodium lactate; 30 mg of potassium chloride; and 20 mg of calcium chloride in a total of 100 ml of distilled water.

Preferably, Hypol 2002 is added to the solution of vascular collagen in a 1:1 volumetric ratio such as 1 ml Hypol 2002 per ml of the collagen solution and the reaction between collagen and polyurethane is allowed to proceed, the reaction proceeding in the mold. In a preferred embodiment the solutions of Hypol 2002 and collagen are mixed at 4°-6° C. and the reaction time is complete within two minutes.

The polyurethane is activated as a function of temperature, releasing $CO_2$. The temperature and hence the rate at which $CO_2$ is released controls the number and size of the $CO_2$ bubbles in the final product, and thus the foaminess, permeability and strength of the prosthesis wall. In a preferred embodiment, the reaction is run at 4°-6° C. and results in a product in which the bubbles are small and uniformly distributed throughout the prosthesis.

A bubble is considered to be small if its diameter is less than 0.2 mm, of medium size if its diameter is between 0.2-0.5 mm, and large if its diameter is 1 mm or greater. Large bubbles are undesirable and tend to lend to failure of the prosthesis at the site of the large bubble.

The molded prosthesis has a compliance at least as good as a human artery where compliance is understood by those in the art to be the ease with which a vessel segment can expand to hold a larger volume. Compliance is generally looked upon as an indicator of the overall health of a given blood vessel. The foam polyurethane-collagen grafts of the invention are considerably more "compliant," that is, "stretchy," than a natural vessel and have the ability to be elongated to twice their original length with not much plastic deformation. Plastic deformation is that phase where a material is stretched beyond its ability to recoil to normal form or to snap back. It is the part of the deformation curve just prior to failure or breakage of the material.

Triton X-100 is a nonionic detergent composed of various polyoxyethylene ethers and other surface-active compounds. Triton X-100 is available commercially and is produced by Rohm & Haas Co. In this invention, Triton X-100 serves only as a surfactant and does not participate in the reaction between collagen and polyurethane. Therefore, other surface active agents which are non-ionic such as Brij, Tween or silicon oils would be useful in this capacity. A surface active compound may not be necessary and may be omitted if desired. The decision on whether or not to include a surface active compound will depend upon the performance of the collagen-polyurethane solution in forming a suitable prosthesis. For example, prostheses made using the synthetic collagen "Vitrogen" (Collagen Corp.), do not require the addition of a surface active compound in the solution forming the molded prosthesis to yield a desirable product.

Heparin serves as an endothelial cell growth factor and as an anticoagulant and is not a required participant in the reaction between collagen and polyurethane. The presence of heparin in the collagen solution at the time of the reaction ensures that the prosthesis will be thoroughly impregnated with the compound. As an endothelial cell growth factor, heparin serves to encourage the establishment of endothelial cells as a confluent endothelial lining of the prosthesis after implantation. When seeded prior to implantation, a lining of endothelial cells reduces the thrombogenicity of a prosthesis (Shindo, S., et al., *J. Vasc. Surg.* 6:325-332 (1987)).

In a highly preferred embodiment, the prosthesis of the invention is an "active" prosthesis as opposed to a "pasive" prosthesis. An "active prosthesis" performs a mechanical function. Examples of mechanical functions include (a) the mechanical function of confined transport of a fluid, and especially blood, (b) the mechanical function of fluid flow regulation, for example, opening and/or closing an aperture, such as a valve, and (c) the mechanical function of expansion and/or contraction in harmony with the physiological demands of the supporting environment, for example, the expansion and contraction requirements of an aortic patch.

The prostheses prepared by the method of the invention can be stored in distilled water with antibiotics, antimycotics and the like to prevent contamination of the graft. Alternatively, the prostheses can be dried and then ethylene oxide sterilized. The prostheses may also be sterilized by gamma radiation.

In one embodiment, the wall thicknesses between the natural biological vessel and the prosthesis are essentially the same. The wall thickness of the prosthesis is limited only by that thickness which is required to provide sufficient mechanical strength so as not to tear, split or produce undesired fluid or hemodynamic flow problems under physiological conditions. It is not necessary to exactly match the thickness of the natural biological vessel with that of the prosthesis.

In a preferred embodiment, a prosthesis is constructed which contains more than one layer of the collagen-polyurethane mixture, each layer surrounding the other. In a highly preferred embodiment, a prosthesis of at least two layers is constructed and the outer layer includes a silicone elastomer in place of the collagen. A prosthesis with two layers can be constructed, for example, by molding the first prosthesis layer around a mandrel and then molding a second layer around the structure of the first prosthesis without removing the mandrel. By this method the two layers are "joined." In addition, those of ordinary skill in the art will recognize other ways of joining two molded layers of the composition of the invention, such as chemically linking two molded units. The advantage of a prosthesis comprising layers of the collagen-polyurethane mixture rather than only one layer is that the layered prosthesis is stronger and provides better protection against potential fluid leakage. An outer layer containing a silicone elastomer or a similar substance which adds strength to the prosthesis is advantageous when it is desired to prevent any tendency of the prosthesis to leak in the desired application. Examples of substances which may be used in place of, or in addition to silicone include other polyurethanes or elastomer polymers with similar elastic properties.

Prostheses comprising layers of the molded collagen-polyurethane mixture may be constructed so that the collagen-polyurethane layers are physically attached to each other or they may be constructed with a layer of a different substance, polymer, mesh or netting between the layers. It is only necessary that, in the final product, the various layers do not separate under physiological conditions. Different layers may be impregnated with different drugs, medicinal substances or other biological agents to provide a localized delivery of these agents to specific surfaces of the prosthesis. The different layers may also comprise compositions with differing rates of biodegradability.

Medicinal substances such as drugs, hormones, immunosuppressants, biological agents and the like may be included in the collagen solution and incorporated into the molded prosthesis structure to provide a localized exposure or a controlled delivery of said substance in the host at the site of the implant. Appropriate antibiotic solutions include penicillin, 10,000 U/ml; streptomycin, 10,000 mcgs/ml; or fungizone, 25 mcgs/ml.

In a preferred embodiment, the conduit of the invention is used for a vascular prosthesis in the implantation of a vascular graft, small diameter vascular graft, atrial patch, prosthetic valve cusp or arterial patch. In another preferred embodiment, the invention is used to replace or graft a blood vessel with a small diameter, especially one less than 5 mm in diameter.

The prosthesis or conduit of the invention is also useful as a ureteral, urethral or biliary prosthesis. As is understood by those skilled in the art, the composition of the invention results in a conduit which would be applicable to any biological drain, catheter, cannula, shunt, tube, or tube-like organ such as the windpipe or intestine.

The prosthesis of the invention is also useful as a soft-tissue substitute for example, in bioartificial systems including endocrine or hepatic transplantation, soft-tissue prothetic materials and bone grafts.

In another embodiment, the composition of the invention is used to create a sustained-release vehicle to deliver a prolonged dose of a compound internally. Such a vehicle would be useful to deliver prolonged, localized doses of drugs, medical agents, biological agents, and the like used in the treatment of many diseases, including heart disease, glaucoma, angina, motion sickness, narcotics addiction, cancer, diabetes, pollen allergies and high blood pressure. In addition, such a vehicle would be useful for the sustained release of such compounds in the digestive system, for example, for weight control; or, for the delayed release of drugs till they passed the stomach. The composition of the invention would also be capable of providing a unit containing a matrix system to prolong the effectiveness of cosmetics, pesticides, fertilizers, detergents, cleaning agents and the like.

When embodied in a layered form, the sustained-release vehicle of the invention may be used to deliver different compounds at different rates or to different sites of action. For example, a compound of interest incorporated into the outer layer of the vehicle may diffuse from the vehicle faster than one contained only in an inner layer. Alternatively, a vehicle may be designed to deliver one drug to the stomach and one to the lower intestine, for example, by incorporating the drug designed for release in the lower intestine into an inner layer of the vehicle and incorporating the drug designed for release in the stomach into the outer layer.

Having now generally described this invention, the same will be better understood by reference to certain examples which are included herein for purposes of illustration only and are not intended to be limiting unless otherwise specified.

EXAMPLE 1

Procedure for Making a Layered Graft of Polyurethane/Collagen/Silicone Elastomer Silicone tubing to be used as the mandrel is placed on a rotating device such as a lathe. Hypol 2002 is mixed with the stock collagen solution in a 1:1 ratio (the stock solution is 1 mg collagen/ml). The polyurethane/collagen mixture is layered onto the rotating mandrel and allowed to cure while continuously rotating, normally for approximately 30 minutes.

A mixture of polyurethane and silicone is made by mixing equal amounts of Hypol 2002 and Dow Corning #92-009 Silicone Dispersion Fluid, then mixing in the Stock Saline Solution (0.9% NaCl, 2 units/ml heparin and 2 ml/liter 0.1% Triton X-100) (without collagen). Each constituent comprises one-third of the total mixture. The polyurethane/silicone mixture is then layered onto the rotating mandrel over the first layer of cured Hypol/collagen and allowed to cure while rotating.

Approximately 4g of Silicone Dispersion #92-009 is mixed with approximately 2-3 g of table salt prior to curing to ensure that the final silicone layer will be porous. The Silicone Dispersion salt mixture is then layered onto the rotating mandrel over the previous layers. This coating is allowed to cure while rotating and takes hours to cure completely. Normally this layer is allowed to cure overnight. The rotation can be terminated after approximately 2 hours after which the silicone elastomer will hold its form without further rotation. The salt does not dissolve in the silicone dispersion and after the layer cures, crystals of salt can be visually observed.

The mandrel-with-graft can now be removed from the lathe and soaked in distilled water to dissolve out the salt. Removing the salt crystals results in a porous material compatible with the uses described in the application. The resultant silicone elastomer layer is porous yet thin and strong enough to resist tearing at the site of sutures.

The graft can now be removed from the mandrel and stored. The graft can be stored dry or it can be stored in the saline stock solution (with antibiotics). If it is stored dry it is necessary to rehydrate the graft prior to use.

EXAMPLE

Tensile Measurements

Graft prototypes were made by hand by smoothly mixing the prepolymer Hypol 2000 with an equal volume of stock solution containing 1 mg/ml collagen dissolved in lactated Ringer's solution (or 0.9% NaCl) containing 2 units/ml heparin and 2 ml/liter 0.1% Triton X-100. A glass rod was used for the mixing and allowed to remain in the test tube as the mandrel for the graft's lumen. Smooth mixing, rather than vigorous shaking, was necessary to avoid generating large bubbles.

After being mixed in a cup using a wooden tongue depressor, the polyurethane-collagen mixture was poured into a tubular mold to react and cure. Virtually any size graft can be made this way. As the mixture foamed, it overflowed the mold through the longitudinal opening through which the fluid was poured. After the material cured, the excess was trimmed off. The graft was then lifted out of the mold on the piece forming the lumen. That piece was then pulled away leaving the tubular cast. Any remaining excess material was again trimmed away.

The samples were tested for their tensile strength by inserting a ring, 0.5 cm in length, cut from the graft into a Tensile Tester (Instron) sample holders.

As shown in FIG. 1, stress and strain testing demonstrated excellent elongation properties (approximately 2x) with very little plastic deformation before material failure. Prosthesis samples which did not have the bubbles uniformly distributed throughout their structure were inferior and gave poor results in the stress and strain testing.

EXAMPLE 3

Compliance Measurements

Figure 2:
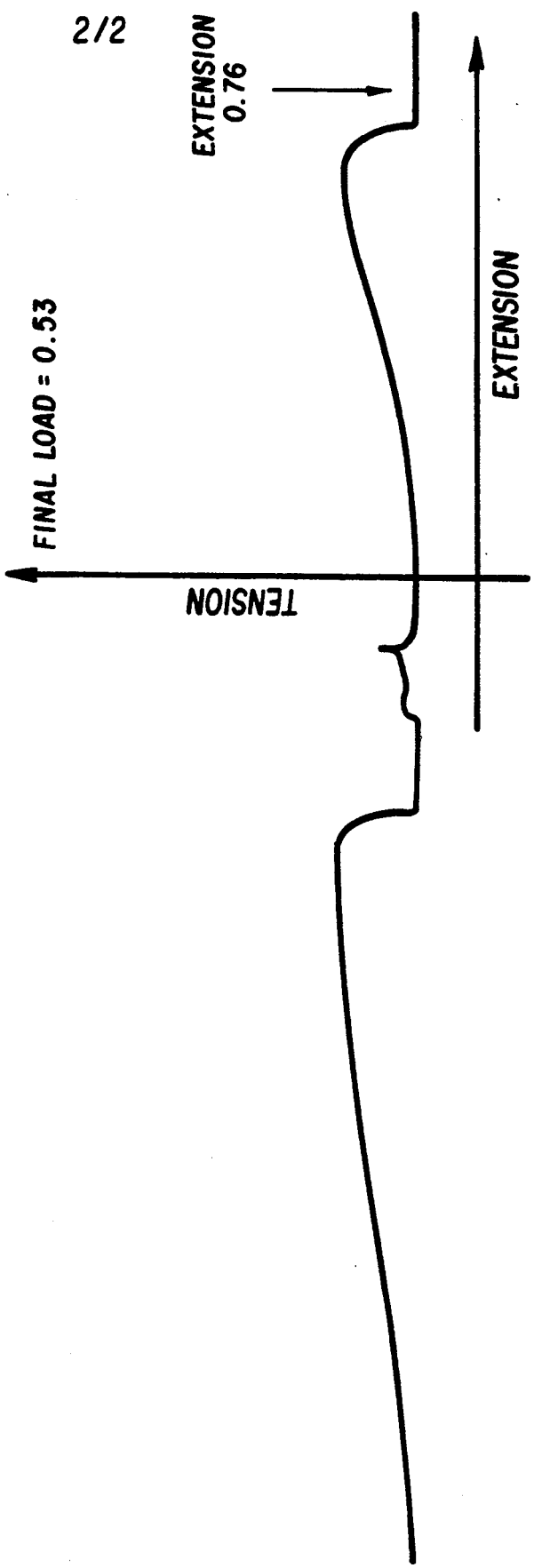
FIG. 2 is a graph representative of results typical of the tensile strength of a polyurethane/collagen graft (1.0 mg/ml collagen), single layer.

Tensile strength and elongation measurements for a prosthesis made as described in Example 1 are shown in FIG. 2. Over a range that is two to three times physiologic, the total graft elongation was approximately 40%, or 4 mm. The experimental grafts produced thus far demonstrate approximately 10% diameter expansion (dynamic compliance) in an in vitro circuit with flow pressure at 150 mm Hg.

EXAMPLE 4

Biological Compatibility of Hypol

Preliminary cell culture experiments were done to examine the cured Hypol 2002 as a host material for endothelial cells. Small discs of cured Hypol 2002 of approximately 2 cm$^2$ were placed into cell culture wells and seeded with canine endothelial cells. The same cell culture procedures were followed as are standard in our laboratory for all cell culture experiments. (Shindo, S., et al., *J. Vasc. Surg.* 6:325-332 (1987)). The cells overgrew the Hypol material and grew to confluence in fairly short order. This indicates that Hypol is a biologically acceptable substrate for endothelial cells and seeded prostheses.

EXAMPLE 5

Animal Implants

Collagen-polyurethane-silicone prostheses as prepared in Example 1 were implanted in the carotid position in six sheep. Grafts subsequently harvested after four weeks were observed to maintain satisfactory integrity and patency for use as vascular prostheses.

Having now fully described this invention, it will be understood by those with skill in the art that the scope may be performed within a wide and equivalent range of conditions, parameters, and the like, without affecting the spirit or scope of the invention or of any embodiment thereof.

What is claimed is:

1. A prosthesis useful for implantation in an animal, wherein said prosthesis comprises:
    at least one layer of a uniform mixture of closed-cell foam polyurethane and collagen in the shape of an elongated hollow body tube, said hollow body tube being open at both ends and defining a confined-flow passageway.

2. The prosthesis of claim 1, wherein said prosthesis further comprises two or more layers of a uniform mixture of foam polyurethane and collagen.

3. The prosthesis of claim 1, wherein said prosthesis further comprises an outer layer which contains a silicone elastomer.

4. The prosthesis of claim 1, wherein the confined-flow passageway has an inner diameter of 10 mm or less.

5. The prosthesis of claim 1, wherein the confined-flow passageway has an inner diameter of 5 m or less.

6. The prosthesis of any one of claims 2-5, wherein said prosthesis contains an antibiotic.

7. The prosthesis of any one of claims 2-5, wherein said prosthesis contains a hormone.

8. The prosthesis of any one of claims 2-5, wherein said prosthesis contains an immunosuppressant agent.

9. A method for implanting a vascular prosthesis which comprises suturing a prosthesis having at least one layer containing a uniform mixture of foam polyurethane and collagen into a blood vessel, tissue or other organ.

10. A method for implanting a ureteral prosthesis which comprises replacing the ureter, or a portion thereof, with a prosthesis having at least one layer containing a uniform mixture of foam polyurethane and collagen.

11. A method for implanting a urethral prosthesis which comprises replacing the urethra, or a portion thereof, with a prosthesis having at least one layer containing a uniform mixture of foam polyurethane and collagen.

12. A method for implanting a biliary prosthesis which comprises replacing the bile duct, or a portion thereof, with a prosthesis having at least one layer containing a uniform mixture of foam polyurethane and collagen.

13. The method of any one of claims 9-12, wherein said prosthesis further comprises two or more layers of a uniform mixture of foam polyurethane and collagen.

14. The method of any one of claims 9-12, wherein said prosthesis further comprises an outer layer which contains a silicone elastomer.

15. The method of any one of claims 9-12, wherein said prosthesis further comprises closed-cell foam polyurethane.

* * * * *